United States Patent [19]

Girijavallabhan et al.

[11] Patent Number: 4,617,300

[45] Date of Patent: Oct. 14, 1986

[54] 2(N-HETEROCYCLYL) PENEMS

[75] Inventors: Viyyoor M. Girijavallabhan, Parsippany; Ashit K. Ganguly, Upper Montclair; Naginbhai Patel, Kearny; Yi-Tsung Liu, Parsippany, all of N.J.

[73] Assignee: Schering Corporation, Kenilworth, N.J.

[21] Appl. No.: 652,707

[22] Filed: Sep. 21, 1984

[51] Int. Cl.$^4$ .................. C07D 499/00; A61K 31/425
[52] U.S. Cl. ..................................... 514/192; 540/201; 540/310; 540/357; 540/360
[58] Field of Search ................. 260/245.2 R, 245.2 T; 514/192

[56] References Cited

U.S. PATENT DOCUMENTS 4,260,618  4/1981  Christensen et al. ............... 424/263
4,272,437  6/1981  Menard et al. .................. 260/239 A

FOREIGN PATENT DOCUMENTS 2013674  8/1979  United Kingdom .

Primary Examiner—Nicholas S. Rizzo
Attorney, Agent, or Firm—Gerald S. Rosen; Thomas D. Hoffman

[57] ABSTRACT

There are disclosed 2(N-heterocyclyl) penems and their pharmaceutically acceptable salts and esters and their use as anti-bacterials.

34 Claims, No Drawings

2(N-HETEROCYCLYL) PENEMS

BACKGROUND OF THE INVENTION

This invention relates to 2-(N-heterocyclyl) penems and their pharmaceutically acceptable salts and pharmaceutically acceptable esters, which compounds possess potent anti-bacterial activity.

There is a continuing need for new antibacterial agents because continued extensive use of effective anti-bacterials gives rise to resistant strains of pathogens.

SUMMARY OF THE INVENTION

This invention provides novel penems substituted in the 2-position by a heterocyclic group wherein a nitrogen of the heterocyclic ring is connected by a bond to the 2 carbon of the penem molecule. The compounds of this invention are anti-bacterial agents.

More particularly, this invention provides compounds represented by the formula

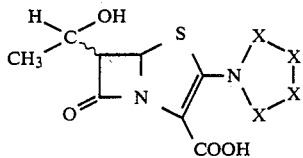

and pharmaceutically acceptable salts and pharmaceutically acceptable esters thereof, in racemic or optically active form, wherein each X independently is

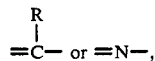

with the proviso that at least one X is

each R is independently selected from hydrogen, lower alkyl, hydroxy, amino lower alkyl, mono- and di-lower alkyl amino lower alkyl, hydroxy lower alkyl, carbamoyloxy lower alkyl, amino, mono- and di-lower alkyl amino, carboxy lower alkyl, carbamoyl lower alkyl, mono- and di-lower alkyl carbamoyl lower alkyl, cyano lower alkyl, halo lower alkyl, carboxy, cyano, hydroxyl imino-methyl, sulfo lower alkyl, lower alkoxy imino-methyl, lower alkoxy, 1(N,N-mono- or di-lower alkyl) hydrazino-2-ylidenyl methyl, carbamoyl amino, mono- and di-lower alkyl carbamoyl amino, lower alkanoyloxy, carbamoyloxy, lower alkanoyl amino, lower alkanoyl amino lower alkyl, N-lower alkylureido, lower alkyl sulfonylamino, sulfonic acid, nitro and 2 adjacent R groups can be connected to form, fused to the five membered heterocyclic ring, a six membered heterocyclic ring of the formula

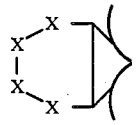

wherein X is as defined herein.

Contemplated within the scope of this invention are aromatic and non-aromatic heterocyclic rings, e.g., imidazoles, triazoles, tetrazoles, purines, imidazolines, and the like.

Preferred compounds of formula I are those in which the nitrogen-containing heterocyclic substituents are unsubstituted and substituted imidazoles, triazoles and tetrazoles, e.g., imidazol-1-yl, 1,2,4-triazol-4-yl, 1,2,4-triazol-1-yl, 1,2,3-triazol-2-yl, 1,2,3-triazol-1-yl, 1,2,3,4-tetrazol-1-yl, 1,2,3,4-tetrazol-2-yl and pyrazol-1-yl.

Preferred R substituents are amino, hydroxy and lower alkyl.

The terms "lower alkyl," "lower alkoxy" and "lower alkanoyl" as used herein means alkyl, alkoxy and alkanoyl groups of 1 to 6 carbon atoms in the alkyl portion and includes branched and straight chains, e.g., methyl, ethyl, propyl, isopropyl, butyl, iso-butyl, tertiary butyl, pentyl, hexyl, neopentyl, methoxy, ethoxy, propoxy, iso-propoxy, butoxy, iso-butoxy, pentoxy, hexoxy, acetyl, propionyl, butyryl, pentanoyl and hexanoyl. "Halo" includes fluorine, chlorine and bromine.

As used herein, "pharmaceutically acceptable salts" means alkali metal salts such as sodium and potassium salts; alkaline earth metal salts such as calcium, magnesium and aluminum salts; amine salts formed from a wide variety of suitable organic amines, i.e., aliphatic, cycloaliphatic, (cyloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N, N'-dibenzylethylenediamine, pyridine, collidine, quinoline, procaine, dibenzylamine, 1-ephenamine and N-alkylpiperidine, acid addition salts formed from mineral acids such as hydrochloric, hydrobromic, hydroiodic, phosphoric or sulfuric acids, or formed from organic carboxylic or sulfonic acids such as trifluoroacetic, para-toluene sulfonic, maleic, acetic, citric, oxalic, succinic, benzoic, tartaric, fumaric, mandelic, ascorbic and malic acids. The compounds of this invention contain a 3-carboxylic group and a basic group (the heterocyclic group) which form an inner salt, i.e., a Zwitterion.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glyclyoxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. Salts of the compound can be formed, for example, by treating with metal compounds such as alkali metal salts of suitable carboxylic acids, or with ammonia or a suitable organic amine, wherein preferably stoichiometric amounts or only a small-excess of the salt-forming agent is used. Acid addition salts of the compound are obtained in the usual manner, for example, by treating with an acid or a suitable anion exchange reagent. Inner salts of the compounds of formula A, i.e., a zwitterion, may be formed by neutralizing salts such as acid addition salts to the isoelectric point. The esters are preparable in a manner analogous to the preparation of the corresponding esters of penicillins and cephalosporins.

Salts may be converted in the usual manner into the free carboxy compounds.

At the 5, 6 and 8 positions of the penem nucleus having chiral atoms, the compounds of this invention may possess 5R, 6S, 8R or 5R, 6R, 8S stereochemistry at those chiral atoms. The preferred absolute stereochemistry for the compounds of this invention at those positions is 5R, 6S, 8R.

DETAILED DESCRIPTION

When tested in standardized microbiological assays, the compounds of this invention are active against such gram-positive organisms as *Staphylococcus epidermis* and *Bacillus subtilis,* and such gram-negative organisms as *E. coli* and *Salmonella* at test levels of 0.1 to 2.0 micrograms/ml. Additionally, they show activity against organisms which produce beta-lactamase, e.g., penicillinase and cephalosporinase, indicating a stability toward those enzymes. For instance, (5R,6S,8R)-2-(imidazol-1-yl)-6-(1-hydroxyethyl) penem-3-carboxylic acid is active against *E. coli* 74081501 TEM-1 (a beta-lactamase producing organism) at 0.5 microgram/ml.

When tested against over sixty organisms, the mean test level against gram-negative organisms was 1.54 micrograms/ml and against gram-positive organisms was 0.27 micrograms/ml.

The compounds of this invention and their metabolites have little or no unpleasant odor.

As anti-bacterial agents, the compounds of this invention are conventionally formulated for oral, parenteral, topical and transdermal use. Thus, this invention includes within its scope pharmaceutical compositions comprising the compounds of this invention in admixture with a pharmaceutically acceptable carrier thereof. In addition, the present invention also provides a method of treating bacterial infections in animals, particularly warm-blooded animals having a susceptible bacterial infection which comprises administering to said animal an anti-bacterial effective amount of a compound of this invention, or a pharmaceutical composition thereof. In the foregoing compositions, the compounds of this invention can be used as the sole active anti-bacterial agent or in combination with other antibacterial agents and/or enzyme inhibitors.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery devices, e.g., transdermal. Parenteral administration is preferred.

Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium suflate; polyvinyl pyrrolidone; polyvinyl alcohol; stearic acid; alkaline earth metal stearates such a magnesium stearate; vegetable oils such as peanut oil, cottonseed oil, sesame oil, olive oil and corn oil; non-ionic, cationic and anionic surfactants; ethylene gylcol polymers; betacyclodextrin; fatty alcohols; hydrolyzed cereal solids; water; polyalkylene gylcols; gums; and petrolatum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dosage of the compounds of this invention which is administered is dependent, on the judgment of the attending clinician taking into account a variety of factors, i.e., the age and weight of the individual being treated, the mode of administration, and the type and severity of the bacterial infection being prevented or reduced and the potency of the specific compound administered. Typically, the dosage administered per day will be in the range of from about 1 to 250 mg/kg and preferably from about 5 to 20 mg/kg in divided dosages. Typically, the dosage will be administered is dosage units containing convenient amounts, for example, 250, 500, 1,000 or 2,000 mg of active ingredient combined with a suitable physiologically acceptable carrier or diluent.

The preferred compounds of this invention are prepared by reacting an azetidinone represented by the formula

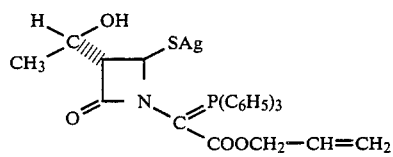

II with bis(trimethylsilyl) acetamide or other known readily removable hydroxy protecting group to protect the hydroxyl group, then with a thiocarbonyl compound represented by the formula

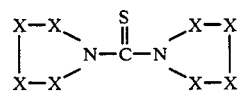

III wherein X is as defined for formula I, to obtain a compound represented by the formula

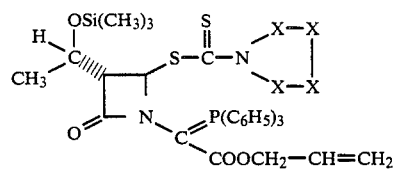

IV wherein X is as defined above.

The above reactions take place in an organic solvent which is inert to the reaction, e.g., methylene chloride.

The compound of Formula IV is then cyclized by heating in an organic solvent such as toluene and the hydroxy group is deprotected by conventional means, e.g., heating with methanol in acetic acid. To obtain a compound represented by the formula

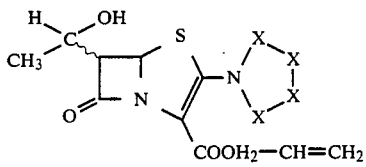

V wherein X is as defined above.

Removal of the allyl group from compound V is effected by the addition of the above allyl ester to a solution containing palladium (zero) and an alkali alkyl-carboxylate, carboxylic acid or aqueous carbonate. This is described by McCombie in U.S. Pat. No. 4,314,942 which is incorporated herein by reference. Under these conditions, removal of the allyl group and formation of the alkali salt or the free acid occurs.

The thiocarbonyl intermediates are known compounds or can be made by known methods disclosed in Larson et. al., J. Org. Chem., 43, 337 (1978). Analogous heterocyclic substituents and substituted heterocyclic substituents can be made by using as the starting material the corresponding substituted silylated derivative. For example, the N-trimethylsilyl derivative of the heterocyclic compound is converted to the corresponding thiocarbonyl by reaction with $CSCl_2$ (thiophosgene) in a carbontetrachloride solvent as shown in the following reaction scheme.

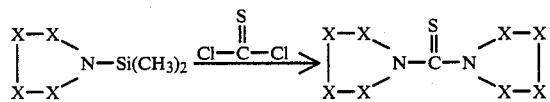

wherein X is as defined for formula I.

The azetidinone intermediate can be prepared, for example, by the following reaction scheme

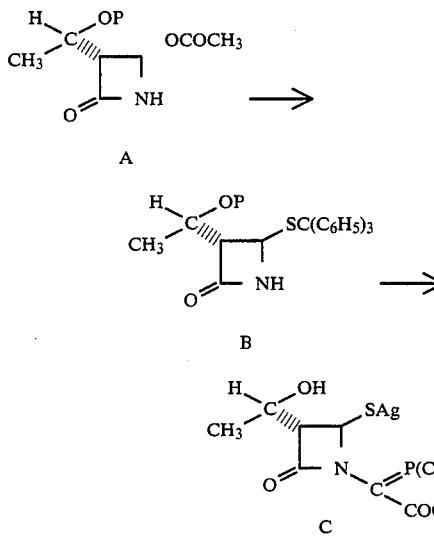

wherein OP is a protected hydroxyl group.

The acetoxy group of compound A is displaced with $—SC(C_6H_5)_3$ by reaction with trityl thiol. The resulting compound B is converted to compound C by reaction with the allyl ester of glyoxylic acid to obtain a compound represented by the formula

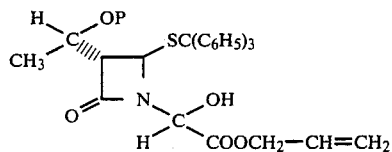

D

The hydroxy group is converted to the corresponding chloro derivative by treatment with a chlorinating agent in an inert organic solvent in the presence or absence of a base.

The chloro compound is then reacted with triphenyl phosphine in an inert organic solvent in the presence of a base to produce the corresponding phosphorane compound represented by the formula

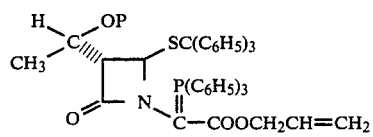

E

The hydroxy protecting group of compound E is removed by conventional means known in the lactam art and the resulting compound is reacted with a reactive silver salt to form compound C.

The following examples illustrate the preparation of the compounds and compositions of this invention.

EXAMPLE 1

Silver 3S,4R)-3-(1-Hydroxyethyl)-1-!Allyl(Triphenylphos-phoranylidene Acetate)1-Azetidin-2-One-4-Thiolate Add 1.15 ml of a 1 molal solution $AgNO_3/1:1$ pyridine/MeOH to a solution of 0.8 gm of compound E (with the hydroxy deprotected) in 5 ml methanol and 1.5 ml $CH_2Cl_2$ in an ice-bath at 0° C. Stir for 1 hour until thin layer chromatography (TLC)(75% EtOAc/hexane) shows no starting material. Remove the solvent, add 25 ml $CH_2Cl_2$, wash with water and dry over $Na_2SO_4$ to obtain the title compound as a yellow solid.

EXAMPLE 2

1,1′ Thiocarbonyl-Di-Pyrazole

Add a solution of 1.43 gm (0.0125 mole) $CSCl_2$ in 5 ml of $CCl_4$ during 1.5 hours with cooling in an ice-bath to a solution of 3.5 gm trimethyl silyl pyrazole in 20 ml $CCl_4$. Continue stirring for 6 hours.

Remove the solvent under vacuum and crystallize the resulting oil by adding seed crystals (prepared by cooling a small amount of the oil in dry ice/acetone) to obtain title compound.

EXAMPLE 3

1,1′ Thiocarbonyl-Di-1,2,4 Triazole

Add a solution of 1.43 gm (0.0125 mole) $CSCl_2$ in 5 ml $CCl_4$ during 1.5 hours to an ice-bath cooled and stirred solution of 3.5 gm (0.025 mole) trimethyl silyl- 1,2,4 triazole in 20 ml $CCl_4$, a yellow solid begins precipitating after about 45 minutes. Stir for 8 hours at room temperature after addition is complete. Isolate the title compound as a yellow solid.

EXAMPLE 4

(5R,6S,8R)2-(Imidazol-1-yl)-6-(1-Hydroxyethyl)-Penem-3-Carboxylic Acid (a) Add 0.12 ml (0.0994 gm, 0.00049 mole) bis(trimethylsilyl)acetamide to a solution of 100 mg (0.00016 mole) of the compound of Example 1 in 5 ml $CH_2Cl_2$. Stir the resulting solution for 0.5 hour at room temperature and remove the $CH_2Cl_2$ solvent under vacuum. Dissolve the resulting residue in 10 ml $CH_2Cl_2$, add 0.057 gm (0.00032 mole) 1,1′-thiocarbonyldiimidazole (available from Aldrich Chemical Co., Milwaukee, Wisc.). Stir the mixture at room temperature for 1 hour. The resulting product, (3S,4R)-3-(1-trimethylsilyloxy ethyl)-1-[allyl(triphenylphosphoranylidene acetate)]-4-imidazol-1-yl thiocarbonyl-azetidin-2-one, was recovered.

(b) Heat a solution of 0.5 gm of the product of part (a) of this example in 50 ml toluene under reflux for three hours. Remove the solvent under vacuum and recover the product, allyl(5R,6S,8R)-2(imidazol-1-yl)-6-(1-trimethylsilyloxyethyl)-penem-3-carboxylate.

(c) Dissolve about 200 mg of the compound made in part (b) of this example in methanol. After about three hours, add acetic acid dropwise until the reaction is complete as determined by TLC (50% ethylacetate/$CH_2Cl_2$) and recover allyl(5R,6S,8R)-2-(imidazol-1-yl)-6-(1-hydroxyethyl)-penem-3-carboxylate (formula V).

NMR: ($CDCl_3$), δ7.8(1H, S), 7–7.2 (2H, M), 5.7–6.0(1H, M), 5–5.3(2H, M), 4.55(2H, d), 4.15(1H, M), 3.75(1H, d of d), 1.3(3H, d).

(d) Add 0.8 ml of 2-ethyl hexanoic acid and 250 mg triphenylphosphine to a solution the compound produced in part (c) of this example. Add to the resulting solution a solution of 100 mg $Pd[P(C_6H_5)_3]$ in 3 ml $CH_2Cl_2$. The reaction is completed within one hour. Recover the product and obtain the title compound as a white solid.

NMR: $D_2O$: δ8.85(1H, broad singlet), 7.57(1H, broad s), 7.4(1H, broad s), 5.8(1H, d), 1.25 (3H, d), between 4 & 4.6 masked by spinning bands of DHO.
MS $[M+H]^+282$.

EXAMPLE 5

(5R,6S,8R) 2-(Pyrazol-1-yl)-6-(1-Hydroxyethyl)-Penem-3-Carboxylic Acid (a) Add 1.2 ml bis-(trimethyl silyl) acetamide to a solution of 1.0 gm of the compound of Example 1 in 25 ml $CH_2Cl_2$. Stir the solution at room temperature for 0.5 hour and then remove the $CH_2Cl_2$ under vacuum. Dissolve the resulting residue in 40 ml $CH_2Cl_2$ and add 0.57 gm 1,1′-thiocarbonyldipyrazole. Stir at room temperature for 2 hours and then recover the product as a yellow oil, (3S,4R)-3-(1-trimethylsilyloxyethyl)-1-[allyl(triphenylphosphoranylidene acetate)]-4-pyrazol-1-yl thiocarbonylazetidin-2-one.

(b) Heat under reflux for 3 hours a solution of 0.5 gm of the product of part (a) of this example in 50 ml toluene. Remove the solvent under vacuum and recover the product, allyl (5R,6S,8R)-2-(pyrazol-1-yl)-6-(1-trimethylsilyl-oxyethyl)penem-3-carboxylate.

(c) Dissolve 0.1 gm of the compound made in part (b) of this example in 15 ml methanol. After 8 hours add 0.25 ml glacial acetic acid to complete the reaction as determined by TLC. Recover the product, allyl (5R,6S,8R)-2-(pyrazol-1-yl)6-(1-hydroxyethyl)penem-3-carboxylate) as a yellow solid.

NMR: c$Dd_3$: d 8.6(1H, d), 7.7(1H, d), 6.4(1H, t), 5.7–6.2(1H, M), 5.6(1H, d), 5.1–5.5(2H, M), 4.7(2H, M), 4.2(1H, quin), 3.8(1H, d of d), 2.8(1H, broad S), 1.3(3H, d).

(d) Add 0.12 ml 2-ethyl hexanoate and 40 mg triphenylphospine to a solution of 80 mg of the compound made in part (c) of this example in 10 ml of $CH_2Cl_2$. Add to the resulting solution a solution of $Pd[P(C_6H_5)_3]_4$ in 1 ml $CH_2Cl_2$. The reaction was completed after 1 hour as determined by TLC. Recover the title compound as a white solid.
MS$[M+H^+]282$.

EXAMPLE 6

(5R,6S,8R)-2(1,2,4 Triazol-1-yl)-6-(1-Hydroxyethyl) Penem-3-Carboxylic Acid (a) Add 0.24 ml bis(trimethylsilyl) acetamide to a solution of 0.2 gm of the compound made in Example 1 in 5 ml dry $CH_2Cl_2$. After 0.5 hour concentrate on a rotary evaporatos and then under high vacuum. Dissolve the resulting oily residue in 5 ml $CH_2Cl_2$ and add to the solution a solution of 116 mg 1,1′ thiocarbonyldi-1,2,4 triazol-1-yl in 1 ml $CH_2Cl_2$. When the reaction is completed as determined by TLC (10% ethylacetate/$CH_2Cl_2$), recover the product as a yellow solid.

(b) Dissolve 50 mg of the compound made in part (a) of this example in 10 ml toluene and heat under reflux for 1 hour to complete the reaction as determined by TLC (10% ethylacetate/$CH_2Cl_2$). Store the recovered product overnight in a refrigerator to cause deprotection of the hydroxy group and obtain allyl(5R,6S,8R)-2(1,2,4-triazol-1-yl)-6(1-hydroxyethyl)penem-3-carboxylate.

NMR: c$Dd_3$: δ9.1(1H, S), 8.0(1H, S), 5.7–5.1(1H, M), 5.65(1H, d), 5.15–5.4(2H, M), 4.7(2H, M), 4.25(1H, M), 3.82(dH, d of d), 2.6(1H, broad S), 1.35(3H, d).

(c) Add 0.03 gm $Pd[P(C_6H_5)_3]_4$ to a solution of 0.23 gm of the compound made in part (b) of this Example, 0.1 gm triphenylphosphine and 0.4 ml ethylhexanoate in 10 ml $CH_2Cl_2$. Stir the resulting solution at room temperature for 2 hours until TLC ($H_2O$, reverse phrase) shows the reaction is complete, to obtain the title compound as a yellowish solid.
MS. $[M+H]^+283$.

The following are representative compounds of this invention that can be prepared following the procedures of Examples 3, 4 and 5 by substituting equivalent amounts of the appropriate thiocarbonyl compound of formula III for those in Examples 3, 4 and/or 5, it being understood that all of the compounds of formula I can also be prepared in the same manner.

1. (5R,6S,8R) 2-(1,2,3,4-tetrazol-1-yl)-6-(1-hydroxyethyl)-penem-3-carboxylic acid.
2. (5R,6S,8R) 2-(1,2,3,4-tetrazol-2-yl)-6-(1-hydroxyethyl)-penem-3-carboxylic acid.
3. (5R,6S,8R) 2-(1,2,4-triazol-4-yl)-6-(1-hydroxyethyl)-penem-3-carboxylic acid.
4. (5R,6S,8R) 2-(purin-9-yl)-6-(1-hydroxyethyl)-penem-3-carboxylic acid.
5. (5R,6S,8R) 2-(5-hydroxymethylimidazol-1-yl)-6-(1-hydroxyethyl)-penem-3-carboxylic acid.
6. (5R,6S,8R) 2-(4-hydroxymethylimidazol-1-yl)-6-(1-hydroxyethyl)-penem-3-carboxylic acid.

7. (5R,6S,8R) 2-(2-hydroxymethylimidazol-1-yl)-6-(1-hydroxyethyl)-penem-3-carboxylic acid.

In the following examples Active Ingredient is (5R,6S,8R) 2-(imidazol-1-yl)-6-(1-hydroxyethyl)penem-3-carboxylic acid or an equivalent amount of any of its pharmaceutically acceptable salts and esters.

It will be appreciated that this compound can be replaced by equivalent amounts of the other compounds of formula I.

EXAMPLE 7

| No. | Ingredient | Capsules mg/tablet | mg/tablet |
|---|---|---|---|
| 1. | Active Ingredient | 250 | 500.0 |
| 2. | Lactose USP | 100 | 50.0 |
| 3. | Corn Starch, Food Grade | 50 | 43.5 |
| 4. | Microcrystalline Cellulose NF | 95 | 50.0 |
| 5. | Magnesium Stearate NF | 5 | 6.5 |
|  | Total | 500 | 650.0 |

Method of Manufacture

Mix Items Nos. 1, 2, 3 and 4 in a suitable mixer for 10-15 minutes. Add Item No. 5 and mix for 1-3 minutes. Fill the mixture into suitable two-piece hard gelatin capsules using encapsulating machine.

EXAMPLE 8

| No. | Ingredient | Tablets mg/tablet | mg/tablet |
|---|---|---|---|
| 1. | Active Ingredient | 250 | 500 |
| 2. | Lactose USP | 57 | 114 |
| 3. | Corn Starch, Food Grade 10% paste in Purified Water | 20 | 40 |
| 4. | Corn Starch, Food Grade | 18 | 39 |
| 5. | Magnesium Stearate NF | 5 | 7 |
|  | Total | 350 | 700 |

Method of Manufacture

Mix Items Nos. 1 and 2 in a suitable mixer for 10-15 minutes. Granulate the mixture with Item No. 3. Pass the wet granulation through a coarse screen (e.g., ¼"), if needed, and dry the wet granules. Mill the dried granules. Combine Item No. 4 and the dried granules and mix for 10-15 minutes. Add Item No. 5 and mix for 1-3 minutes. Compress the mixture to appropriate size and weight on a suitable tablet machine.

EXAMPLE 9

| Injectable Powder | g/vial | g/vial |
|---|---|---|
| Active Ingredient | 0.5 | 1.0 |

Add sterile water for injection or bacteriostatic water for injection for reconstitution.

EXAMPLE 10

| Ingredient | Injectable Solution mg/ml |
|---|---|
| Active Ingredient | 500 |
| Methylparaben | 1.8 |
| Propylparaben | 0.2 |
| Sodium Bisulfite | 3.2 |

| Ingredient | -continued Injectable Solution mg/ml |
|---|---|
| Disodium Edetate | 1.5 |
| Sodium Sulfate | 2.6 |
| Water for Injection q.s. ad | 1.0 ml |

Method of Manufacture

1. Dissolve parabens in a portion (85% of the final volume) of the water for injection at 65°-70° C.
2. Cool to 25°-35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22 micron membrane and fill into appropriate containers.
6. Terminally sterilize the units by autoclaving.

EXAMPLE 11

| Injectable Powder | g/vial |
|---|---|
| Active Ingredient | 1.00 |
| Sodium Citrate | 0.05 | pH is adjusted to 6.2 using 0.1N citric acid solution. Add sterile water for injection or bacteriostatic water for injection for reconstitution.

We claim:

1. Compounds represented by the formula

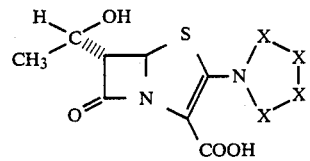

and pharmaceutically acceptable salts and pharmaceutically acceptable esters thereof in racemic or optically active form, wherein each X independently is

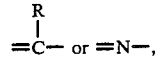

with the proviso that at least one X is

each R is independently selected from hydrogen, lower alkyl, hydroxy, amino lower alkyl, mono- and di-lower alkyl amino lower alkyl, hydroxy lower alkyl, carbamoyloxy lower alkyl, amino, mono- and di-lower alkyl amino, carboxy lower alkyl, carbamoyl lower alkyl, mono-and di-lower alkyl carbamoyl lower alkyl, cyano lower alkyl, halo lower alkyl, carboxy, cyano, hydroxyiminomethyl, sulfo lower alkyl, lower alkoxyimino-methyl, lower alkoxy, 1-(N,N-mono- or di-lower alkyl) hydrazino-2-ylidenyl methyl, carbamoyl amino, mono- and di-lower alkyl carbamoyl amino lower alkanoyloxy, carbamoyloxy, lower alkanoyl amino, lower alkanoyl amino lower alkyl, N-lower alkyl ureido, lower alkyl sulfonyl amino, sulfonic acid, nitro, and 2 adjacent R groups can be connected to form, fused to the five membered heterocyclic ring, a six membered heterocyclic ring of the formula

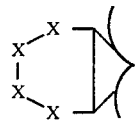

wherein X is as defined herein.

2. A compound of claim 1 wherein

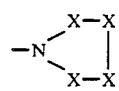

is substituted and unsubstituted imidazol-1-yl; 1,2,4-triazol-4-yl; 1,2,4-triazol-1-yl; 1,2,3,4-tetrazol-1-yl; 1,2,3,4-tetrazol-2-yl; or pyrazol-1-yl; wherein the substituents are independently amino, hydroxy or lower alkyl.

3. A compound of claim 1 which is (5R,6S,8R) 2-(imidazol-1-yl)-6-(1-hydroxyethyl)penem-3-carboxylic acid.

4. A compound of claim 1 which is (5R,6S,8R) 2-(pyrazol-1-yl)-6-(1-hydroxyethyl)penem-3-carboxylic acid.

5. A compound of claim 1 which is (5R,6S,8R) 2-(1,2,4 triazol-1-yl)-6-(1-hydroxy-ethyl)penem-3-carboxylate.

6. A compound of claim 1 which is (5R,6S,8R) 2-(1,2,3,4-tetrazol-1-yl)-6-(1-hydroxyethyl)-penem-3-carboxylic acid.

7. A compound of claim 1 which is (5R,6S,8R) 2-(1,2,3,4-tetrazol-2-yl)-6-(1-hydroxyethyl)-penem-3-carboxylic acid.

8. A compound of claim 1 which is (5R,6S,8R) 2-(1,2,4-triazol-4-yl)-6-(1-hydroxyethyl)-penem-3-carboxylic acid.

9. A compound of claim 1 which is (5R,6S,8R) 2-(purin-9-yl)-6-(1-hydroxyethyl)-penem-3-carboxylic acid.

10. A compound of claim 1 which is (5R,6S,8R) 2-(5-hydroxymethylimidazol-1-yl)-6-(1-hydroxyethyl)-penem-3-carboxylic acid.

11. A compound of claim 1 which is (5R,6S,8R) 2-(4-hydroxymethylimidazol-1-yl)-6-(1-hydroxyethyl)-penem-3-carboxylic acid.

12. A compound of claim 1 which is (5R,6S,8R) 2-(2-hydroxymethylimidazol-1-yl)-6-(1-hydroxyethyl)-penem-3-carboxylic acid.

13. A pharmaceutical composition comprising an anti-bacterial effective amount of a compound of claim 1 in admixture with a pharmaceutically acceptable carrier therefor.

14. A composition according to claim 13 wherein said anti-bacterial compound is (5R,6S,8R) 2-(imidazol-1-yl)-6-(1-hydroxyethyl)penem-3-carboxylic acid.

15. A composition according to claim 13 wherein said anti-bacterial compound is (5R,6S,8R) 2-(pyrazol-1-yl)-6-(1-hydroxyethyl)penem-3-carboxylic acid.

16. A composition according to claim 13 wherein said anti-bacterial compound is (5R,6S,8R) 2-(1,2,4-triazol-1-yl)-6-(1-hydroxyethyl)penem-3-carboxylate.

17. A composition according to claim 13 wherein said anti-bacterial compound is (5R,6S,8R) 2-(1,2,3,4-tetrazol-1-yl)-6-(1-hydroxyethyl)-penem-3-carboxylic acid.

18. A composition according to claim 13 wherein said anti-bacterial compound is (5R,6S,8R) 2-(1,2,3,4-tetrazol-2-yl)-6-(1-hydroxyethyl)-penem-3-carboxylic acid.

19. A composition according to claim 13 wherein said anti-bacterial compound is (5R,6S,8R) 2-(1,2,4-triazol-4-yl)-6-(1-hydroxyethyl)-penem-3-carboxylic acid.

20. A composition according to claim 13 wherein said anti-bacterial compound is (5R,6S,8R) 2-(purin-9-yl)-6-(1-hydroxyethyl)-penem-3-carboxylic acid.

21. A composition according to claim 13 wherein said anti-bacterial compound is (5R,6S,8R) 2-(5-hydroxymethylimidazol-1-yl)-6-(1-hydroxyethyl)-penem-3-carboxylic acid.

22. A composition according to claim 13 wherein said anti-bacterial compound is (5R,6S,8R) 2-(4-hydroxymethylimidazol-1-yl)-6-(1-hydroxyethyl)-penem-3-carboxylic acid.

23. A composition according to claim 13 wherein said anti-bacterial compound is (5R,6S,8R) 2-(2-hydroxymethylimidazol-1-yl)-6-(1-hydroxyethyl)-penem-3-carboxylic acid.

24. A method of treating bacterial infections in patients in need of such treatment which comprises administering an anti-bacterial effective amount of a compound of claim 1.

25. The method of claim 24 wherein the compound administered is (5R,6S,8R)-2-(imidazol-1-yl)-6-(1-hydroxyethyl)penem-3-carboxylic acid.

26. The method of claim 24 wherein the compound administered is (5R,6S,8R)-2-(pyrazol-1-yl)-6-(1-hydroxyethyl)penem-3-carboxylate.

27. The method of claim 24 wherein the compound administered is (5R,6S,8R)-2-(triazol-1-yl)-6-(1-hydrodxyethyl)penem-3-carboxylate.

28. The method of claim 24 wherein the compound administered is (5R,6S,8R) 2-(1,2,3,4-tetrazol-2-yl)-6-(1-hydroxyethyl)-penem-3-carboxylic acid.

29. The method of claim 24 wherein the compound administered is (5R,6S,8R) 2-(1,2,4-triazol-4-yl)-6-(1-hydroxyethyl)-penem-3-carboxylic acid.

30. The method of claim 24 wherein the compound administered is (5R,6S,8R) 2-(purin-9-yl)-6-(1-hydroxyethyl)-penem-3-carboxylic acid.

31. The method of claim 24 wherein the compound administered is (5R,6S,8R) 2-(5-hydroxymethylimidazol-1-yl)-6-(1-hydroxyethyl)-penem-3-carboxylic acid.

32. The method of claim 24 wherein the compound administered is (5R,6S,8R) 2-(4-hydroxymethylimidazol-1-yl)-6-(1-hydroxyethyl)-penem-3-carboxylic acid.

33. The method of claim 24 wherein the compound administered is (5R,6S,8R) 2-(2-hydroxymethylimidazol-1-yl)-6-(1-hydroxyethyl)-penem-3-carboxylic acid.

34. The method of claim 24 wherein the administration is parenteral.

* * * * *